(12) United States Patent
Jones et al.

(10) Patent No.: US 10,435,645 B2
(45) Date of Patent: Oct. 8, 2019

(54) ORGANOLEPTIC COMPOUNDS

(71) Applicant: INTERNATIONAL FLAVORS & FRAGRANCES INC., New York, NY (US)

(72) Inventors: Paul D. Jones, Aberdeen, NJ (US); Edward Mark Arruda, Easton, PA (US)

(73) Assignee: International Flavors & Fragrances Inc., New York, NY (US)

(*) Notice: Subject to any disclaimer, the term of this patent is extended or adjusted under 35 U.S.C. 154(b) by 105 days.

(21) Appl. No.: 15/730,891

(22) Filed: Oct. 12, 2017

(65) Prior Publication Data

US 2018/0171263 A1    Jun. 21, 2018

Related U.S. Application Data

(60) Provisional application No. 62/436,523, filed on Dec. 20, 2016.

(51) Int. Cl.
| | | |
|---|---|---|
| *C11B 9/00* | (2006.01) |
| *C07C 59/205* | (2006.01) |
| *C07C 69/757* | (2006.01) |
| *C11D 3/50* | (2006.01) |

(52) U.S. Cl.
CPC .......... *C11B 9/0019* (2013.01); *C07C 59/205* (2013.01); *C07C 69/757* (2013.01); *C07C 2601/14* (2017.05); *C07C 2601/16* (2017.05); *C11D 3/50* (2013.01)

(58) Field of Classification Search
CPC ...................................... C11B 9/0019
See application file for complete search history.

(56) References Cited

U.S. PATENT DOCUMENTS 4,629,805 A * 12/1986 Sprecker ................ C08K 5/101
                                                         131/276

FOREIGN PATENT DOCUMENTS

EP          0810213 A2    12/1997

OTHER PUBLICATIONS

EPO Extended Search Report dated Dec. 20, 2017 for Application No. EP 17199443.7.

* cited by examiner

*Primary Examiner* — Arrie L Reuther
(74) *Attorney, Agent, or Firm* — XuFan Tseng; Martin Zhang; Elizabeth M. Stover

(57) ABSTRACT

The present invention relates to the novel use of a carboxylate compound as a fragrance material.

19 Claims, No Drawings

ORGANOLEPTIC COMPOUNDS

STATUS OF RELATED APPLICATION

This application claims priority to U.S. Provisional Patent Application No. 62/436,523, filed Dec. 20, 2016, the contents hereby incorporated by reference as if set forth in its entirety.

FIELD OF THE INVENTION

The present invention relates to new chemical entities and the incorporation and use of the new chemical entities as fragrance materials.

BACKGROUND OF THE INVENTION

There is an ongoing need in the fragrance industry to provide new chemicals to give perfumers and other persons the ability to create new fragrances for perfumes, colognes and personal care products. Those with skill in the art appreciate how differences in the chemical structure of the molecule can result in significant differences in the odor, notes and characteristics of a molecule. These variations and the ongoing need to discover and use the new chemicals in the development of new fragrances allow the perfumers to apply the new compounds in creating new fragrances.

SUMMARY OF THE INVENTION

The present invention provides the unexpected novel use of ethyl 4-methyl-2-oxocyclohexane-1-carboxylate in enhancing, improving or modifying the fragrance of perfumes, colognes, toilet water, fabric care products, personal products and the like.

More specifically, the present invention relates to ethyl 4-methyl-2-oxocyclohexane-1-carboxylate represented by Formula I set forth below:

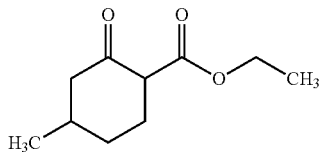

Formula I

The compound of Formula I also exists in a tautomeric form, ethyl 2-hydroxy-4-methylcyclohex-1-ene-1-carboxylate, represented by Formula II set forth below:

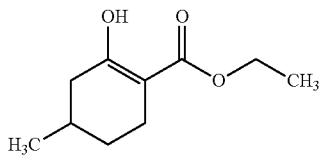

Formula II

Formula I and II are capable of existing in a state of equilibrium as a mixture. Accordingly, the compounds of the present invention are represented by Formula I, which is intended to encompass Formula I, Formula II, and a mixture thereof.

Another embodiment of the present invention relates to a fragrance composition comprising an olfactory acceptable amount of the compounds provided above.

Another embodiment of the present invention relates to a fragrance product comprising an olfactory acceptable amount of the compounds provided above.

Another embodiment of the present invention relates to a method of improving, enhancing or modifying a fragrance formulation through the addition of an olfactory acceptable amount of the compounds provided above.

These and other embodiments of the present invention will be apparent by reading the following specification.

DETAILED DESCRIPTION OF THE INVENTION

Those with skill in the art will recognize that the compounds of the present invention are further capable of existing in enantiomeric forms such as ethyl rel-(1R,4S)-4-methyl-2-oxocyclohexane-1-carboxylate and ethyl rel-(1R,4R)-4-methyl-2-oxocyclohexane-1-carboxylate. It is intended herein that the compounds described herein include isomeric mixtures of such compounds, as well as those isomers that may be separated using techniques known to those having skill in the art. Suitable techniques include chromatography such as high performance liquid chromatography, referred to as HPLC, particularly silica gel chromatograph, and gas chromatography trapping known as GC trapping. Yet, commercial versions of such products are mostly offered as mixtures. The preparation of the compounds of the present invention is detailed in the Examples. Materials were purchased from Aldrich Chemical Company unless noted otherwise.

The compounds of the present invention, for example, possess strong and complex fruity, nutty, sweet and floral notes. The use of the compounds of the present invention is widely applicable in current perfumery products, including the preparation of perfumes and colognes, the perfuming of personal care products such as soaps, shower gels, and hair care products, fabric care products, air fresheners, and cosmetic preparations. The present invention can also be used to perfume cleaning agents, such as, but not limited to detergents, dishwashing materials, scrubbing compositions, window cleaners and the like.

In these preparations, the compounds of the present invention can be used alone or in combination with other perfuming compositions, solvents, adjuvants and the like. The nature and variety of the other ingredients that can also be employed are known to those with skill in the art. Many types of fragrances can be employed in the present invention, the only limitation being the compatibility with the other components being employed. Suitable fragrances include but are not limited to fruits such as almond, apple, cherry, grape, pear, pineapple, orange, strawberry, raspberry; musk, flower scents such as lavender-like, rose-like, iris-like, carnation-like. Other pleasant scents include herbal and woodland scents derived from pine, spruce and other forest smells. Fragrances may also be derived from various oils, such as essential oils, or from plant materials such as peppermint, spearmint and the like.

A list of suitable fragrances is provided in U.S. Pat. No. 4,534,891, the contents of which are incorporated by reference as if set forth in its entirety. Another source of suitable fragrances is found in *Perfumes, Cosmetics and Soaps*, Second Edition, edited by W. A. Poucher, 1959. Among the fragrances provided in this treatise are acacia, cassie, chypre, cyclamen, fern, gardenia, hawthorn, heliotrope, honeysuckle, hyacinth, jasmine, lilac, lily, magnolia, mimosa, narcissus, freshly-cut hay, orange blossom, orchid, reseda, sweet pea, trefle, tuberose, vanilla, violet, wallflower, and the like.

The compounds of the present invention can be used in combination with a complementary fragrance compound. The term "complementary fragrance compound" as used herein is defined as a fragrance compound selected from the group consisting of 2-[(4-methylphenyl)methylene]-heptanal (Acalea), iso-amyl oxyacetic acid allylester (Allyl Amyl Glycolate), (3,3-dimethylcyclohexyl)ethyl ethyl propane-1,3-dioate (Applelide), (E/Z)-1-ethoxy-1-decene (Arctical), 2-ethyl-4-(2,2,3-trimethyl-3-cyclo-penten-1-yl)-2-buten-1-ol (Bacdanol), 2-methyl-3-[(1,7,7-trimethylbicyclo[2.2.1]hept-2-yl)oxy] exo-1-propanol (Bornafix), 1,2,3,5,6,7-hexahydro-1,1,2,3,3-pentamethyl-4H-inden-4-one (Cashmeran), trimethylcyclopentenylmethyloxabicyclooctane (Cassiffix), 1,1-dimethoxy-3,7-dimethyl-2,6-octadiene (Citral DMA), 3,7-dimethyl-6-octen-1-ol (Citronellol), 3A,4,5,6,7,7A-hexahydro-4,7-methano-1H-inden-5/6-yl acetate (Cyclacet), 3A,4,5,6,7,7A-hexahydro-4,7-methano-1H-inden-5/6-yl propinoate (Cyclaprop), 3A,4,5,6,7,7A-hexahydro-4,7-methano-1G-inden-5/6-yl butyrate (Cyclobutanate), 1-(2,6,6-trimethyl-3-cyclohexen-1-yl)-2-buten-1-one (Delta Damascone), 3-(4-ethylphenyl)-2,2-dimethyl propanenitrile (Fleuranil), 3-(O/P-ethylphenyl) 2,2-dimethyl propionaldehyde (Floralozone), tetrahydro-4-methyl-2-(2-methylpropyl)-2H-pyran-4-ol (Floriffol), 1,3,4,6,7,8-hexahydro-4,6,6,7,8,8-hexamethylcyclopenta-gamma-2-benzopyran (Galaxolide), 1-(5,5-dimethyl-1-cyclohexen-1-yl)pent-4-en-1-one (Galbascone), E/Z-3,7-dimethyl-2,6-octadien-1-yl acetate (Geranyl Acetate), α-methyl-1,3-benzodioxole-5-propanal (Helional), 1-(2,6,6-trimethyl-2-cyclohexen-1-yl)-1,6-heptadien-3-one (Hexalon), (Z)-3-hexenyl-2-hydroxybenzoate (Hexenyl Salicylate, CIS-3), 4-(2,6,6-trimethyl-2-cyclohexen-1-yl)-3-buten-2-one (Ionone α), 1-(1,2,3,4,5,6,7,8-octahydro-2,3,8,8-tetramethyl-2-naphthalenyl)-ethan-1-one (Iso E Super), methyl 3-oxo-2-pentylcyclopentaneacetate (Kharismal), 2,2,4-trimethyl-4-phenyl-butanenitrile (Khusinil), 3,4,5,6,6-pentamethylhept-3-en-2-one (Koavone), 3/4-(4-hydroxy-4-methyl-pentyl) cyclohexene-1-carboxaldehyde (Lyral), 3-methyl-4-(2,6,6-trimethyl-2-cyclohexen-1-yl)-3-buten-2-one (Methyl Ionone γ), 1-(2,6,6-trimethyl-2-cyclohexen-1-yl) pent-en-3-one (Methyl Ionone α Extra, Methyl Ionone N), 3-methyl-4-phenylbutan-2-ol (Muguesia), cyclopentadec-4-en-1-one (Musk Z4), 3,3,4,5,5-pentamethyl-11,13-dioxatricyclo[7.4.0.0<2,6>]tridec-2(6)-ene (Nebulone), 3,7-dimethyl-2,6-octadien-1-yl acetate (Neryl Acetate), 3,7-dimethyl-1,3,6-octatriene (Ocimene), ortho-tolylethanol (Peomosa), 3-methyl-5-phenylpentanol (Phenoxanol), 1-methyl-4-(4-methyl-3-pentenyl) cyclohex-3-ene-1-carboxaldehyde (Precyclemone B), 4-methyl-8-methylene-2-adamantanol (Prismantol), 2-ethyl-4-(2,2,3-trimethyl-3-cyclopenten-1-yl)-2-buten-1-ol (Sanjinol), 2-methyl-4-(2,2,3-trimethyl-3-cyclopenten-1-yl)-2-buten-1-ol (Santaliff), Terpineol, 2,4-dimethyl-3-cyclohexene-1-carboxaldehyde (Triplal), decahydro-2,6,6,7,8,8-hexamethyl-2H-indeno[4,5-B]furan (Trisamber), 2-tert-butylcyclohexyl acetate (Verdox), 4-tert-butylcyclohexyL acetate (Vertenex), acetyl cedrene (Vertofix), 3,6/4,6-dimethylcyclohex-3-ene-1-carboxaldehyde (Vertoliff), and (3Z)-1-[(2-methyl-2-propenyl)oxy]-3-hexene (Vivaldie).

Complexity of odor notes refers to the presence of multiple and/or mixed but defined odors rather than a single note or a few easily identifiable notes. High levels of complexity are also assigned to compounds that possess ambiguous and somehow hard-to-define notes because of direct contribution or the many olfactive combinations of odors produced. Fragrance materials of high level complexity are considered having unusual and high quality.

The term "alkyl" means a linear or branched saturated monovalent hydrocarbon, e.g., methyl, ethyl, propyl, 2-propyl, butyl (including all isomeric forms), pentyl (including all isomeric forms), hexyl (including all isomeric forms), and the like. The term "alkenyl" means a linear or branched unsaturated, aliphatic hydrocarbon containing at least one carbon-carbon double bond. The term "alkylene" refers to bivalent alkyl. Examples include —CH$_2$—, —CH$_2$CH$_2$—, —CH$_2$CH$_2$CH$_2$—, —CH$_2$(CH$_3$)CH$_2$—, —CH$_2$CH$_2$CH$_2$CH$_2$—, and the like.

The term "tautomers" means compounds that are interconvertible by migration of a hydrogen atom, accompanied by a switch of a single bond and adjacent double bond. The tautomers of the present invention include compounds of Formula I or II which are capable of existing in a state of equilibrium. The exact ratio of the tautomers depends on several factors, such as temperature, solvent, and pH. All tautomeric forms of the compounds disclosed herein and mixtures thereof are included within the scope of each formula.

The terms "fragrance formulation", "fragrance composition", and "perfume composition" mean the same and refer to a consumer composition that is a mixture of compounds including, for example, alcohols, aldehydes, ketones, esters, ethers, lactones, nitriles, natural oils, synthetic oils, and mercaptans, which are admixed so that the combined odors of the individual components produce a pleasant or desired fragrance. The fragrance formulation of the present invention is a consumer composition comprising a compound of the present invention. The fragrance formulation of the present invention comprises a compound of the present invention and further a complementary fragrance compound as defined above.

The term "fragrance product" means a consumer product containing a fragrance ingredient that adds fragrance or masks malodor. Fragrance products may include, for example, perfumes, colognes, bar soaps, liquid soaps, shower gels, foam baths, cosmetics, skin care products such as creams, lotions and shaving products, hair care products for shampooing, rinsing, conditioning, bleaching, coloring, dyeing and styling, deodorants and antiperspirants, feminine care products such as tampons and feminine napkins, baby care products such as diapers, bibs and wipes, family care products such as bath tissues, facial tissues, paper handkerchiefs or paper towels, fabric products such as fabric softeners and fresheners, air care products such as air fresheners and fragrance delivery systems, cosmetic preparations, cleaning agents and disinfectants such as detergents, dishwashing materials, scrubbing compositions, glass and metal cleaners such as window cleaners, countertop cleaners, floor and carpet cleaners, toilet cleaners and bleach additives, washing agents such as all-purpose, heavy duty, and hand washing or fine fabric washing agents including laundry detergents and rinse additives, dental and oral hygiene products such as toothpastes, tooth gels, dental flosses, denture cleansers, denture adhesives, dentifrices, tooth whitening and mouthwashes, health care and nutritional products and food products such as snack and beverage products. The fragrance product of the present invention is a consumer product that contains a compound of the present invention. The fragrance product of the present invention contains a compound of the present invention and further a complementary fragrance compound as defined above.

The term "improving" in the phrase "improving, enhancing or modifying a fragrance formulation" is understood to mean raising the fragrance formulation to a more desirable character. The term "enhancing" is understood to mean making the fragrance formulation greater in effectiveness or providing the fragrance formulation with an improved character. The term "modifying" is understood to mean providing the fragrance formulation with a change in character.

The term "olfactory acceptable amount" is understood to mean the amount of a compound in a fragrance formulation, wherein the compound will contribute its individual olfactory characteristics. However, the olfactory effect of the fragrance formulation will be the sum of effect of each of the fragrance ingredients. Thus, the compound of the present invention can be used to improve or enhance the aroma characteristics of the fragrance formulation, or by modifying the olfactory reaction contributed by other ingredients in the formulation. The olfactory acceptable amount may vary depending on many factors including other ingredients, their relative amounts and the olfactory effect that is desired.

The amount of the compounds of the present invention employed in a fragrance formulation varies from about 0.005 to about 70 weight percent, preferably from 0.005 to about 50 weight percent, more preferably from about 0.5 to about 25 weight percent, and even more preferably from about 1 to about 10 weight percent. Those with skill in the art will be able to employ the desired amount to provide desired fragrance effect and intensity. In addition to the compounds of the present invention, other materials can also be used in conjunction with the fragrance formulation to encapsulate and/or deliver the fragrance. Some well-known materials are, for example, but not limited to, polymers, oligomers, other non-polymers such as surfactants, emulsifiers, lipids including fats, waxes and phospholipids, organic oils, mineral oils, petrolatum, natural oils, perfume fixatives, fibers, starches, sugars and solid surface materials such as zeolite and silica. Some preferred polymers include polyacrylate, polyurea, polyurethane, polyacrylamide, polyester, polyether, polyamide, poly(acrylate-co-acrylamide), starch, silica, gelatin and gum Arabic, alginate, chitosan, polylactide, poly(melamine-formaldehyde), poly(urea-formaldehyde), or a combination thereof.

When used in a fragrance formulation these ingredients provide additional notes to make a fragrance formulation more desirable and noticeable, and add the perception of value. The odor qualities found in these materials assist in beautifying and enhancing the finished accord as well as improving the performance of the other materials in the fragrance.

In addition, the compounds of the present invention are also surprisingly found to provide superior ingredient performance and possess unexpected advantages in malodor counteracting applications such as body perspiration, environmental odor such as mold and mildew, bathroom, and etc. The compounds of the present invention substantially eliminate the perception of malodors and/or prevent the formation of such malodors, thus, can be utilized with a vast number of functional products.

Examples of the functional products are provided herein to illustrate the various aspects of the present invention. However, they do not intend to limit the scope of the present invention. The functional products may include, for example, a conventional room freshener (or deodorant) composition such as room freshener sprays, an aerosol or other spray, fragrance diffusers, a wick or other liquid system, or a solid, for instance candles or a wax base as in pomanders and plastics, powders as in sachets or dry sprays or gels, as in solid gel sticks, clothes deodorants as applied by washing machine applications such as in detergents, powders, liquids, whiteners or fabric softeners, fabric refreshers, linen sprays, closet blocks, closet aerosol sprays, or clothes storage areas or in dry cleaning to overcome residual solvent notes on clothes, bathroom accessories such as paper towels, bathroom tissues, sanitary napkins, towellets, disposable wash cloths, disposable diapers, and diaper pail deodorants, cleansers such as disinfectants and toilet bowl cleaners, cosmetic products such as antiperspirant and deodorants, general body deodorants in the form of powders, aerosols, liquids or solid, or hair care products such as hair sprays, conditioners, rinses, hair colors and dyes, permanent waves, depilatories, hair straighteners, hair groom applications such as pomade, creams and lotions, medicated hair care products containing such ingredients as selenium sulphide, coal tar or salicylates, or shampoos, or foot care products such as foot powders, liquids or colognes, after shaves and body lotions, or soaps and synthetic detergents such as bars, liquids, foams or powders, odor control such as during manufacturing processes, such as in the textile finishing industry and the printing industry (inks and paper), effluent control such as in processes involved in pulping, stock yard and meat processings, sewage treatment, garbage bags, or garbage disposal, or in product odor control as in textile finished goods, rubber finished goods or car fresheners, agricultural and pet care products such as dog and hen house effluents and domestic animal and pet care products such as deodorants, shampoo or cleaning agents, or animal litter material and in large scale closed air systems such as auditoria, and subways and transport systems.

Thus, it will be seen that the composition of the invention is usually one in which the malodor counteractant is present together with a carrier by means of which or from which the malodor counteractant can be introduced into air space wherein the malodor is present, or a substrate on which the malodor has deposited. For example, the carrier can be an aerosol propellant such as a chlorofluoro-methane, or a solid such as a wax, plastics material, rubber, inert powder or gel. In a wick-type air freshener, the carrier is a substantially odorless liquid of low volatility. In several applications, a composition of the invention contains a surface active agent or a disinfectant, while in others, the malodor counteractant is present on a fibrous substrate. In many compositions of the invention there is also present a fragrance component which imparts a fragrance to the composition. The fragrances stated above can all be employed.

Malodor counteracting effective amount is understood to mean the amount of the inventive malodor counteractant employed in a functional product that is organoleptically effective to abate a given malodor while reducing the combined intensity of the odor level, wherein the given malodor is present in air space or has deposited on a substrate. The exact amount of malodor counteractant agent employed may vary depending upon the type of malodor counteractant, the type of the carrier employed, and the level of malodor counteractancy desired. In general, the amount of malodor counteractant agent present is the ordinary dosage required to obtain the desired result. Such dosage is known to the skilled practitioner in the art. In a preferred embodiment, when used in conjunction with malodorous solid or liquid functional products, e.g., soap and detergent, the compounds of the present invention may be present in an amount ranging from about 0.005 to about 50 weight percent, preferably from about 0.01 to about 20 weight percent, and more preferably from about 0.05 to about 5 weight percent, and when used in conjunction with malodorous gaseous functional products, the compounds of the present invention may be present in an amount ranging from about 0.1 to 500 mg per cubic meter of air.

The following are provided as specific embodiments of the present invention. Other modifications of this invention will be readily apparent to those skilled in the art. Such modifications are understood to be within the scope of this invention. As used herein all percentages are weight percent unless otherwise noted, ppm is understood to stand for parts per million, L is understood to be liter, mL is understood to be milliliter, g is understood to be gram, Kg is understood to be kilogram, mol is understood to be mole, mmol is understood to be millimole, psig is understood to be pound-force per square inch gauge, and mmHg be millimeters (mm) of mercury (Hg). IFF as used in the examples is understood to mean International Flavors & Fragrances Inc., New York, N.Y., USA.

Example I

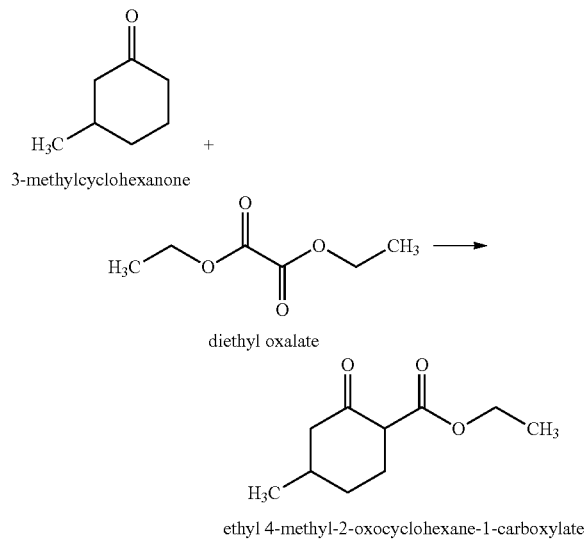

Preparation of Ethyl 4-methyl-2-oxocyclohexane-1-carboxylate (Formula I)

A mixture of 3-methylcyclohexanone (173 g, 1.54 mol) and diethyl oxalate (225 g, 1.54 mol) was fed to a solution of sodium ethoxide ($C_2H_5ONa$) (21% in ethanol) (500 g, 1.54 mol) over 2 hours while the temperature was maintained at 25° C. After the feed was complete, the reaction was aged at 25° C. for additional 2 hours. The reaction mixture was acidified with aqueous sulfuric acid ($H_2SO_4$) (75.6 g, 0.8 mol) in water (500 mL). The aqueous layer was removed and the organic layer was heated to 150° C. with simultaneous removal of low boiling components. Gas evolution began when the reaction reached 130° C. as evidenced via a mineral oil bubbler. The reaction was aged for about 4 hours until gas evolution ceased. The crude product was distilled to afford a 1:2 keto-enol tautomeric mixture of ethyl 4-methyl-2-oxocyclohexane-1-carboxylate (Formula I) and ethyl 2-hydroxy-4-methylcyclohex-1-ene-1-carboxylate (Formula II) as a clear oil (120 g) having a boiling point of 89-90° C. at a pressure of 4 mmHg. Ethyl 4-methyl-2-oxocyclohexane-1-carboxylate further contained a 1:1 isomeric mixture of ethyl rel-(1R,4S)-4-methyl-2-oxocyclohexane-1-carboxylate and ethyl rel-(1R,4R)-4-methyl-2-oxocyclohexane-1-carboxylate.

Ethyl 4-methyl-2-oxocyclohexane-1-carboxylate had the following NMR spectral characteristics:

$^1$H NMR (400 MHz, $CDCl_3$): 4.16 (q, J=7.1 Hz, 2H), 3.32-3.35 (m, 1H), 1.64-2.50 (m, 7H), 1.25 (t, J=7.1 Hz, 3H), 0.93-1.08 (m, 3H).

Ethyl 2-hydroxy-4-methylcyclohex-1-ene-1-carboxylate had the following NMR spectral characteristics:

$^1$H NMR (400 MHz, $CDCl_3$): 12.15 (s, 1H), 4.16 (q, J=7.1 Hz, 2H), 1.60-2.48 (m, 7H), 1.25 (t, J=7.2 Hz, 3H), 0.95 (d, J=6.5 Hz, 3H)

Ethyl 2-hydroxy-4-methylcyclohex-1-ene-1-carboxylate was described as having balsamic, hay-like, nutty and sweet notes.

Ethyl rel-(1R,4S)-4-methyl-2-oxocyclohexane-1-carboxylate had the following NMR spectral characteristics:

$^1$H NMR (400 MHz, $CDCl_3$): 12.15 (s, 30% of 1H), 4.09-4.23 (m, 2H), 3.24-3.30 (m, 70% of 1H), 1.61-2.46 (m, 6H), 1.39-1.46 (m, 1H), 1.25 (t, J=7.1 Hz, 30% of 3H), 1.23 (t, J=7.1 Hz, 70% of 3H), 0.97 (d, J=6.7 Hz, 70% of 3H), 0.95 (d, J=6.7 Hz, 30% of 3H)

Ethyl rel-(1R,4S)-4-methyl-2-oxocyclohexane-1-carboxylate was described as having fruity, sweet and winey notes.

Ethyl rel-(1R,4R)-4-methyl-2-oxocyclohexane-1-carboxylate had the following NMR spectral characteristics:

$^1$H NMR (400 MHz, $CDCl_3$): 12.15 (s, 30% of 1H), 4.09-4.25 (m, 2H), 3.26 (ddd, J=12.6, 5.8, 0.9 Hz, 70% of 1H), 1.62-2.48 (m, 6H), 1.06-1.40 (m, 1H), 1.25 (t, J=7.1 Hz, 30% of 3H), 1.23 (t, J=7.1 Hz, 70% of 3H), 0.99 (d, J=6.3 Hz, 70% of 3H), 0.95 (d, J=6.5 Hz, 30% of 3H)

Ethyl rel-(1R,4R)-4-methyl-2-oxocyclohexane-1-carboxylate was described as having balsamic, hay-like, nutty, sweet and tobacco-like notes.

The mixture of ethyl 4-methyl-2-oxocyclohexane-1-carboxylate and ethyl 2-hydroxy-4-methylcyclohex-1-ene-1-carboxylate was described as having fruity, nutty, sweet and floral notes.

Example II

Following carboxylates were similarly prepared.

Methyl 4-methyl-2-oxocyclohexane-1-carboxylate

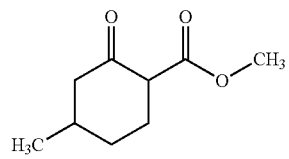

$^1$H NMR (500 MHz, $CDCl_3$): 12.10 (s, 80% of 1H), 3.73 (s, 80% of 3H), 3.72 (s, 20% of 3H), 3.25-3.28 (m, 20% of 1H), 1.68-2.47 (m, 6H), 0.82-1.52 (m, 4H)

Ethyl 4,4-dimethyl-2-oxocyclohexane-1-carboxylate

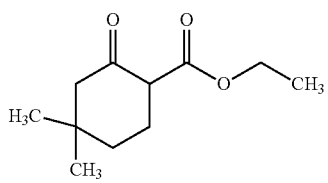

$^1$H NMR (500 MHz, CDCl$_3$): 12.17 (s, 1H), 4.18 (q, J=7.1 Hz, 2H), 2.22 (tt, J=6.5, 1.5 Hz, 2H), 2.02 (s, 2H), 1.35 (t, J=6.5 Hz, 2H), 1.28 (t, J=7.3 Hz, 3H), 0.93 (s, 6H)

Propyl 4-methyl-2-oxocyclohexane-1-carboxylate

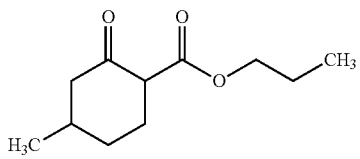

1H NMR (500 MHz, CDCl$_3$): 12.12 (s, 80% of 1H), 3.87-4.22 (m, 2H), 3.20-3.27 (m, 20% of 1H), 2.34-2.42 (m, 20% of 1H), 2.20-2.33 (m, 80% of 2H), 2.05-2.15 (m, 1H), 1.95-2.01 (m, 20% of 1H), 1.80-1.95 (m, 1H), 1.55-1.75 (m, 4H), 0.74-1.52 (m, 7H)

Ethyl 5-methyl-2-oxocyclohexane-1-carboxylate

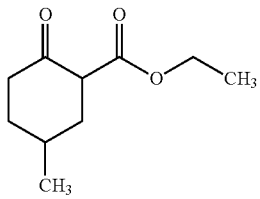

$^1$H NMR (400 MHz, CDCl$_3$): 12.16 (s, 88% of 1H), 3.84-4.46 (m, 2H), 3.37 (dd, J=13.3, 5.5 Hz, 4% of 1H), 3.27 (ddd, J=5.7, 4.0, 1.6 Hz, 8% of 1H), 1.32-2.53 (m, 7H), 1.23 (t, J=7.1 Hz, 3H), 0.94 (d, J=6.5 Hz, 3H)

Ethyl 1-allyl-4-methyl-2-oxocyclohexane-1-carboxylate

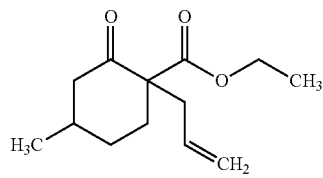

$^1$H NMR (500 MHz, CDCl$_3$): 5.58-5.84 (m, 1H), 4.93-5.12 (m, 2H), 4.05-4.23 (m, 2H), 2.05-2.63 (m, 6H), 1.65-1.92 (m, 2H), 1.29-1.51 (m, 1H), 1.21 (t, J=7.3 Hz, 67% of 3H), 1.20 (t, J=7.1 Hz, 33% of 3H), 0.95 (d, J=6.6 Hz, 33% of 3H), 0.92 (d, J=6.6 Hz, 67% of 3H)

Methyl 2-oxocycloheptane-1-carboxylate

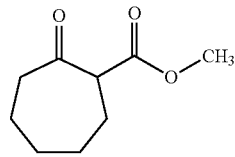

$^1$H NMR (400 MHz, CDCl$_3$): 12.64 (s, 17% of 1H), 3.73 (s, 17% of 3H), 3.70 (s, 83% of 3H), 3.54 (dd, J=10.3, 4.0 Hz, 83% of 1H), 1.36-2.68 (m, 10H)

Ethyl 2-oxocyclooctane-1-carboxylate

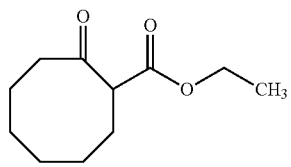

$^1$H NMR (500 MHz, CDCl$_3$): 12.5 (s, 65% of 1H), 4.19 (q, J=7.1 Hz, 65% of 2H), 4.12 (q, J=7.1 Hz, 35% of 2H), 3.54 (dd, J=11.2, 4.0 Hz, 35% of 1H), 2.56-2.60 (m, 35% of 1H), 2.46-2.47 (m, 35% of 1H), 2.36-2.38 (m, 65% of 2H), 2.31-2.34 (m, 65% of 2H), 1.35-2.15 (m, 65% of 8H and 35% of 10H), 1.27 (t, J=7.1 Hz, 65% of 3H), 1.21 (t, J=7.1 Hz, 35% of 3H)

Example III

The fragrance properties of the above compounds were evaluated using (i) odor strength of 0 to 10, where 0=none, 1=very weak, 5=moderate, 10=extremely strong; and (ii) level of complexity, where 0=none, 1=very low, 5=moderate, 10=extremely high. Averaged scores are reported in the following:

| Compound | Odor Profile | Strength | Complexity |
|---|---|---|---|
| methyl 4-methyl-2-oxocyclohexane-1-carboxylate | Anisic, nutty, dry hay-like and animalic but fecal | 5 | 5 |
| ethyl 4-methyl-2-oxocyclohexane-1-carboxylate | Fruity, nutty, sweet and floral | 9 | 10 |

-continued

| Compound | Odor Profile | Strength | Complexity |
|---|---|---|---|
| ethyl 4,4-dimethyl-2-oxocyclohexane-1-carboxylate | Slightly fruity, lactonic and hay-like. Spicy and woody but oily | 3 | 3 |
| propyl 4-methyl-2-oxocyclohexane-1-carboxylate | Fruity, nutty, hay-like but weak and thin. Slightly earthy and oily | 4 | 4 |
| ethyl 5-methyl-2-oxocyclohexane-1-carboxylate | Fruity of apple- and banana-like as well as bubble gum-like and artificial | 4 | 5 |
| ethyl 1-allyl-4-methyl-2-oxocyclohexane-1-carboxylate | Herbaceous, fresh, balsamic, piney, woody and spicy with a burnt quality | 5 | 5 |
| methyl 2-oxocycloheptane-1-carboxylate | Solventy of kerosene-like. Fruity but synthetic and chemical | 4 | 3 |
| ethyl 2-oxocyclooctane-1-carboxylate | Fruity and hay-like but with a solventy quality | 5 | 5 |

Ethyl 4-methyl-2-oxocyclohexane-1-carboxylate exhibited unique and particularly desirable odor profile, which is strong and complex, superior to all other analog compounds. Such advantageous properties are unexpected.

Example IV

Establishment of Malodor Models:
The sweat, mold/mildew, bathroom and smoke malodor models were prepared based on Applicants' proprietary formulations for assessing the effectiveness of various malodor counteractants.
Preparation of Test Samples:
Two aluminum dishes were placed in an 8 oz glass jar. A malodor material was pipetted into one aluminum dish, and ethyl 4-methyl-2-oxocyclohexane-1-carboxylate (prepared above in EXAMPLE I) diluted in a solvent (1%) or a solvent alone control was pipetted into the other aluminum dish. The jar was then capped and the samples were allowed to equilibrate for one hour before the testing.
Testing Procedure:
Test samples were presented in a blind and random order to 15-18 internal panelists (consisting of men/women with an age range of 25 to 55). However, different odor samples were arranged in an alternative order (for example, sweat, mold/mildew, sweat, mold/mildew, and etc.).
The panelists were instructed to take the steps of i) sniff jars containing only the malodor materials for familiarization prior to the testing; ii) uncap a jar; iii) place their noses at a distance of about 3-4 inches above the opening; iv) take short sniffs for 3 seconds; and v) enter a rating of overall intensity and malodor intensity on a handheld computer.
The overall and malodor intensity was rated using the Labeled Magnitude Scale (LMS) [Green, et al., Chemical Senses, 21(3), June 1996, 323-334]. Percent malodor reduction ("% MOR") represents the perceived reduction in mean malodor intensity of the sample containing the malodor in the presence of a malodor counteractant relative to the negative control (Malodor Alone).
Results and Discussion:
The mean ranks of the malodor coverage for the above test were as follows:

| Compound (1%) | Malodor | % MOR |
|---|---|---|
| ethyl 4-methyl-2-oxocyclohexane-1-carboxylate | Sweat | 79.17 |
| | Mold/Mildew | 65.32 |
| | Bathroom | 82.55 |
| | Smoke | 31.65 |

Ethyl 4-methyl-2-oxocyclohexane-1-carboxylate was demonstrated effective in counteracting various types of malodors.

What is claimed is:
1. A fragrance formulation containing an olfactory acceptable amount of ethyl 4-methyl-2-oxocyclohexane-1-carboxylate, a tautomer thereof, or a mixture thereof.
2. The fragrance formulation of claim 1, wherein the olfactory acceptable amount is from about 0.005 to about 50 weight percent of the fragrance formulation.
3. The fragrance formulation of claim 1, wherein the olfactory acceptable amount is from about 0.5 to about 25 weight percent of the fragrance formulation.
4. The fragrance formulation of claim 1, wherein the olfactory acceptable amount is from about 1 to about 10 weight percent of the fragrance formulation.
5. The fragrance formulation of claim 1 further comprising a polymer.
6. The fragrance formulation of claim 5, wherein the polymer is selected from the group consisting of polyacrylate, polyurea, polyurethane, polyacrylamide, polyester, polyether, polyamide, poly(acrylate-co-acrylamide), starch, silica, gelatin and gum Arabic, alginate, chitosan, polylactide, poly(melamine-formaldehyde), poly(urea-formaldehyde) and a combination thereof.
7. A fragrance product containing the fragrance formulation of claim 1.
8. The fragrance product of claim 7, wherein the fragrance product is selected from the group consisting of a perfume, a cologne, toilet water, a cosmetic product, a personal care product, a fabric care product, a cleaning product and an air freshener, a bar soap, a liquid soap, a shower gel, a foam bath, a cosmetic, a skin care product, a hair care product, a deodorant, an antiperspirant, a feminine care product, a baby care product, a family care product, a fabric product, an air care product, a fragrance delivery system, a cosmetic preparation, a cleaning agent, a disinfectant, a washing agent, a dental and oral hygiene product, a health care and nutritional product and a food product.
9. The fragrance product of claim 8, wherein the cleaning product is selected from the group consisting of a detergent, a dishwashing material, a scrubbing composition, a glass cleaner, a metal cleaner, a countertop cleaner, a floor cleaner, a carpet cleaner, a toilet cleaner and a bleach additive.
10. The fragrance product of claim 8, wherein the washing agent is selected from the group consisting of a laundry detergent and a rinse additive.
11. A method of improving, enhancing or modifying a fragrance formulation through the addition of an olfactory acceptable amount of ethyl 4-methyl-2-oxocyclohexane-1-carboxylate, a tautomer thereof, or a mixture thereof.

12. The method of claim 11, wherein the olfactory acceptable amount is from about 0.005 to about 50 weight percent of the fragrance formulation.

13. The method of claim 11, wherein the olfactory acceptable amount is from about 0.1 to about 25 weight percent of the fragrance formulation.

14. The method of claim 11, wherein the olfactory acceptable amount is from about 0.5 to about 10 weight percent of the fragrance formulation.

15. A method of counteracting a malodor in an air space or a substrate comprising the step of introducing to the air space or the substrate a composition comprising a malodor counteracting effective amount of ethyl 4-methyl-2-oxocyclohexane-1-carboxylate, a tautomer thereof, or a mixture thereof.

16. The method of claim 15, wherein the malodor counteracting effective amount is from about 0.01 to about 20 weight percent of the substrate.

17. The method of claim 15, wherein the malodor counteracting effective amount is from about 0.05 to about 10 weight percent of the substrate.

18. The method of claim 15, wherein the malodor counteracting effective amount is from about 0.2 milligrams to about 2 grams per cubic meter of air in the air space.

19. The method of claim 15, wherein the malodor counteracting effective amount is from about 4 milligrams to about 0.2 grams per cubic meter of air in the air space.

* * * * *